United States Patent [19]

Milligan et al.

[11] 4,329,501

[45] May 11, 1982

[54] SYNTHESIS OF ALKYL AMINO BENZENES FROM ALKYL DIAMINO BENZENES

[75] Inventors: Barton Milligan, Coplay; Roland E. Grandin, Alburtis, both of Pa.

[73] Assignee: Air Products and Chemicals, Inc., Allentown, Pa.

[21] Appl. No.: 195,565

[22] Filed: Oct. 9, 1980

[51] Int. Cl.³ ........................ C07C 85/00; C07C 85/20
[52] U.S. Cl. ................................. 564/305; 564/437
[58] Field of Search ........................... 564/437, 305

[56] References Cited

U.S. PATENT DOCUMENTS 3,522,310 7/1970 Cross et al. .................... 564/436 X
3,532,754 10/1970 Brown ................................ 564/436
3,686,314 8/1972 Bacha et al. .................... 564/424 X

OTHER PUBLICATIONS

CRC, "Handbook of Chemistry and Physics", 52nd Edition, pp. C-513 and C-517, (1971-1972).

*Primary Examiner*—John Doll
*Attorney, Agent, or Firm*—Russell L. Brewer; E. Eugene Innis; James C. Simmons

[57] ABSTRACT

The conversion of alkyl diaminobenzenes to the alkyl amino benzenes is carried out by contacting the alkyl diamino benzene with hydrogen in the presence of a nonsupported cobalt catalyst. Optionally, the reaction is carried out in the presence of water so that the water insoluble product formed can be separated from the water soluble reactants and by-products.

9 Claims, No Drawings

SYNTHESIS OF ALKYL AMINO BENZENES FROM ALKYL DIAMINO BENZENES

TECHNICAL FIELD

This invention relates to to the catalytic deamination of alkyl diamino benzenes.

BACKGROUND OF PRIOR ART

The catalytic deamination of alkyl diamino benzenes to alkyl amino benzenes, particularly the catalytic deamination of toluene diamine to toluidine has been achieved by effecting the hydrogenation in the presence of a base promoted cobalt oxide catalyst. In this type of process ring hydrogenation has been a significant problem particularly where the catalyst consists of a cobalt oxide-calcium oxide-sodium carbonate material.

U.S. Pat. No. 3,532,754 discloses an improvement in the catalytic deamination process of diamino benzenes and uses a supported cobalt catalyst to effect the deamination. A cobalt hydrogenation catalyst supported on kieselguhr, alumina, silica, carbon or various other supports, and preferably promoted with sodium carbonate or an alkaline earth oxide, is used.

It is also known that the hydrogenolysis of o-toluidine to toluene can be affected over a nickel catalyst. However, the use of a nickel catalyst generally results in substantial ring hydrogenation.

SUMMARY OF THE INVENTION

This invention relates to an improvement in a process for producing alkyl amino benzenes by the catalytic deamination of alkyl diamino benzenes. The basic process comprises contacting an alkyl diamino benzene with hydrogen in the presence of a hydrogenation catalyst under conditions sufficient for effecting deamination and the improvement of this invention resides in utilizing an unsupported cobalt metal as the catalyst, the cobalt catalyst being present in 'a proportion sufficient to effect the deamination.

In another embodiment of the invention, the catalytic deamination is carried out in the presence of water using an insoluble catalyst. In this embodiment, the reduction is carried out to form a water insoluble product phase and aqueous phase and then the insoluble product is separated from the aqueous phase. This procedure eliminates an energy consuming distillation required in the prior art to recover product.

Quite unexpectedly, it was found that the use of an unsupported cobalt catalyst resulted in high yields of an alkyl amino benzene, particularly m-toluidine, when used for deaminating 2,3- and 3,4-toluene diamine reactants. In addition, by using an unsupported catalyst, the reaction can be carried out in the presence of water as noted. Further, the use of a cobalt metal catalyst, and preferably not containing alkaline earth components can be recovered using ferromagnetic techniques and recycled for reuse by water washing.

DESCRIPTION OF THE PREFERRED EMBODIMENTS

In the process of the instant invention, 1-alkyl-2,3-diamino benzenes and 1-alkyl-3,4-diamino benzenes, or mixtures thereof, are catalytically hydrogenated to produce the corresponding 1-alkyl-2, 3- or 4- aminobenzenes. The alkyl diamino benzenes are represented by the formulae:

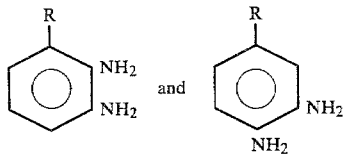

where R is an alkyl group of from about 1 to about 10 carbon atoms, e.g. methyl, propyl, isobutyl, and the like. Specific examples of alkyl diamino benzenes are the vicinal toluene diamines, namely 1-methyl-2,3-diamino benzene, 1-methyl-3,4-diamino benzene; the corresponding 1-ethyl 2,3- and 3,4-diamino benzenes and so on as represented by the formulae.

In carrying out the process, the catalytic deamination of the alkyl diamino benzene can be conducted in the presence of an inert solvent such as toluene, benzene, xylene, hexane, cyclohexane and the like as used in the prior art. Unlike the prior art, though, the use of a non-supported catalyst or a catalyst supported on a component substantially inert to water under alkaline conditions, as described herein, permits the process to be carried out in the presence of water as well as organic solvent as used in the prior art. The ability to carry out the deamination in water permits easy recovery of product from the reactants, and for this reason it is preferred. Easy recovery is achievable since the reactants are water soluble and the product is substantially water insoluble. Thus during hydrogenation, the reactants are converted to a water insoluble phase which can be continuously removed from the reaction. If catalyst is present in this phase, it can be removed by filtration or ferromagnetic techniques.

The temperature of the deamination can vary over a wide range so long as it is effective to achieve deamination. But, generally, the temperature is between about 175° to 250° C., and preferably 220° to 230° C., particularly where the reaction mixture is a mixture of the vicinal toluene diamines. When the temperature falls below 220°, e.g. 200° C., there is a noticeable drop in reaction rate. Pressures of from about 100 to 7,000 psig, and preferably 1,000 to 1,800 are used in the process. Such pressures are conventional in the art.

The significant advantage of this catalytic deamination process is in the utilization of a specific material as the catalyst, namely, an unsupported cobalt metal. The cobalt metal is included in the reaction in a proportion sufficient for effecting deamination, and generally it is used in a proportion to provide from about 1 to 50 (grams) cobalt metal per mole of alkyl diamino benzene reactant. In the catalytic deamination of a vicinal toluene diamine, the proportion of cobalt metal normally used is from about 5 to 15 (grams) per mole of vicinal toluene diamine.

The cobalt metal suited for practicing the invention can be prepared from virtually any cobalt salt in the plus 2 or 3 valence state which is reducible with hydrogen. Reduction can be carried out prior to contact with the toluene diamine or during the reduction of toluene diamine. One of the preferred techniques in forming the catalyst is to first form a complex of cobalt (II) nitrate hexahydrate with ammonia and then reduce the resulting brown precipitate with hydrogen in the presence of the vicinal toluene diamine. Examples of cobalt salts for deamination include cobalt acetate, cobalt nitrate in the form of an ammonia complex, and cobalt oxide. Although the cobalt salts can optionally be promoted with alkaline earth metals, e.g. calcium oxide in a proportion of from 50 to 200% of the cobalt metal; generally though, alkaline earth metals reduce the reaction rate and result in lower conversions. For these reasons, the catalyst does not utilize these alleged promoters.

The following examples are provided to illustrate the invention.

EXAMPLE 1

A series of deamination reactions was carried out in an Autoclave Engineers 300 ml autoclave reactor equipped with a magnetically driven stirrer. Dual heater elements were installed on the autoclave to permit good temperature control.

The procedure generally involved adding 24.4 g of reaction mixture consisting of 90% 2,3- and 3,4-toluenediamine in a weight ratio of 37/63 and the balance toluidine, and other isomers of toluene diamine to an inert solvent in the autoclave. After the reaction mixture was added to the autoclave, a specified amount of catalyst was added to the reaction mixture and the autoclave closed and pressurized to 1500 psi twice with nitrogen to check for leaks and to remove oxygen. After purging with nitrogen, the autoclave was pressurized to 1500 psig with hydrogen, and after purging with hydrogen, the reactor was repressurized with hydrogen to an initial preselected pressure. At that time stirring was commenced. After reaction, external heat was removed and the hydrogen pressure recorded. Unreacted hydrogen was vented.

The products then were recovered from the autoclave and the catalyst removed by filtration. The products then were analyzed using a gas chromatograph (GC).

Table I below provides the conditions and results for each run, e.g. temperature °C., pressure (psig), change from initial to final hydrogen pressure, i.e. change pressure, catalyst type and amount (PR after the catalyst refers to reduction of the catalyst with hydrogen prior to contact with toluene diamine), solvent, and GC area percent of the ortho (O%) meta (m%) and para (p%) isomers of total toluidine product. MCH refers to both methylcyclohexane and methylcyclohexylamine in GC area percent. HAS refers to the hydrogen absorption rate in moles/hr.

TABLE I

| Run | Temp. °C. | Initial Pressure | Change Pressure | Solvent/g | Catalyst/g | Reaction Time/hr. | Yield GC % o-% | p % | m % | MCH | HAS |
|---|---|---|---|---|---|---|---|---|---|---|---|
| *1 | 225 | 600 | 475 | Toluene, 60 | 5.1 g CoO 8g CaO 3g Na$_2$CO$_3$ | 3.25 | 33 | 17 | 36 | 9.9 | 0.08 |
| *2 | 175–200° C. | 600 | 300 | Toluene, 60 | CaO 3g Na$_2$CO$_3$ | 3.75 at 175° C. 3.0 at 200° C. | 8 | 17 | 30 | 3.3 | 0.035 |
| *3 | 225 | 600 | 475 | Toluene, 40 | CaO 3g Na$_2$CO$_3$ | 3.25 | 16.8 | 22.5 | 37.8 | 3.7 | 0.09 |
| 4 | 225 | 600 | 475 | Neat | CaO 3g Na$_2$CO$_3$ | 3.75 | 30 | 17 | 35 | 5.9 | 0.05 |
| 5 | 225 | 600 | 350 | Toluene, 60 | 10.4 g (0.39%) Harshaw CO-127 | 65 | 24.1 | 21.7 | 36.1 | 3.7 | 0.01 |
| 6 | 225 | 600 | 0 | Toluene, 60 | 5.1 g CoO | 3.5 | — | — | — | — | — |
| 7 | 225 | 600 | 450 | Toluene, 60 | 5.1 g CoO, 8g CaO | 3.5 | 33 | 15 | 36 | 9.6 | — |
| 8 | 225 | 600 | — | Toluene, 60 | 5.1 g CoO, 3G Na$_2$ | 3 | — | — | — | — | — |
| 9 | 225 | 600 | 0 | H$_2$O, 60 | Raney Cu 3 ml | — | — | — | — | — | — |
| 10 | 225 | 600 | 100 | H$_2$O, 60 | 5.1 g CoO, 8g CaO | 21 | — | — | — | — | — |
| 11 | 225 | 1300 | 625 | Neat | 12.8 g CoO,31.1g CaO 11 g Na$_2$CO$_3$ | 1.5 | 18.9 | 12.7 | 28.3 | 18.1 | 0.22 |
| 12 | 225 | 1800 | 225 | Neat | 12.8 g Ni203 31.1g CaO, 11 g Na$_2$CO$_3$ | 2 | 14.4 | 13.1 | 273 | 6.1 | 0.13 |
| 13 | 225 | 1800 | 100 | Neat | 31 g Cu Cromite Cu-1402P Harshaw | 25 | 0.5 | 1.1 | 1.1 | 1.5 | — |
| 14 | 225 | 1800 | 300 | Distilled H$_2$O, 50 | 5.1 g Ni$_2$O$_3$8g CaO, 3 g Na$_2$CO$_3$ | | 0.4 | 0.4 | 0.5 | — | — |
| 15 | 225 | 1800 | 475 | Distilled H$_2$O,25 | Raney Nickel (3ml) | | 4.1 | 9.3 | 9.2 | — | 0.02 |
| 16 | 225 | 1800 | 900 | Conc NH$_4$OH/25 ml | 12 g Co(NH$_3$)(H$_2$O)$_y$ (NO$_3$)$_2$ | 16 | 26.1 | 18.2 | 30.3 | 17.1 | 0.002 |
| 17 | 225 | 1800 | 900 | Conc NH$_4$OH/25 ml | 12 g Co(NH$_3$) (H$_2$O)$_y$ (NO$_3$)$_2$ 4 | 25.1 | 18.0 | 29.6 | 12.7 | | 0.03 |
| 18 | 225 | 1800 | 425 | Conc NH$_4$OH/25 ml | 4 g Co(NH$_3$)(H$_2$O)$_y$ (NO$_3$)$_2$ | | | | | | |
| 19 | 225 | 1800 | 325 | Distilled H$_2$O 30 g | 2.6 g Co Metal from Runs 16 & 17 | 19.5 | 14.9 | 16.5 | 46.2 | 1.6 | 0.02 |
| 20 | 225 | 1800 | 500 | Conc NH$_4$OH,25 ml | 1.5 Co Metal from Runs 16 & 17 | 13 | 6.7 | 14.4 | 34.1 | 1.0 | 0.17 |
| 21 | 225 | 1800 | 175 | Distilled H$_2$O,30 | 0.8 g Co Metal | 15 | 2.4 | 5.1 | 12.4 | 0.4 | 0.004 |
| 22 | 200 | 2590 | 275 | Conc NH$_4$OH,30 ml | 4 g Co(NH$_3$)$_x$(H$_2$O)$_y$ (NO$_3$)$_2$ | 15 | 2.8 | 4.2 | 9.7 | 0.4 | 0.004 |
| 23 | 225 | 2500 | 400 | Conc NH4OH, 30 ml | 14 g Co (NH3)6Cl3 | 18 | 0.5 0.6 | 0.4 | — | — | |
| 24 | 225 | 1800 | 1050 | Ca(OH)$_2$5 at soln, 30 ml | 19.4 g Co (H$_2$O)$_6$ (NO$_3$)$_2$ | 16 | 28 | 6 | 32.3 | 18.5 | 0.008 |
| 25 | 225 | 600 | 275 | H$_2$O, 60 | Co metal-Run 2 | 6.5 | 5 | 26 | 35.8 | 3.6 | 0.02 |
| 26 | 225 | 600 | 275 | Toluene, 60 | Co metal-Run 1 | 9.5 | 22 | 18 | 34.9 | 7.8 | 0.02 |
| 27 | 225 | 1800 | 0 | H$_2$O, 25 | 5 g CoO, 8 g Bao PR | 4 | 0.7 | 0.8 | 0.8 | 0.1 | — |
| 28 | 225 | 1800 | 600 | H$_2$O, 30 | 5.1 g CoO, 8 g MgO, Pr | 21.5 | 19.2 | 14.0 | 21.9 | 13.9 | 0.02 |
| 29 | 225 | 1800 | 175 | H$_2$O, 30 | 5 g CoCl$_2$ 8 g BACl$_2$ | 16.5 | 0.7 | 0.9 | 0.6 | — | — |

TABLE I-continued

| Run | Temp. °C. | Initial Pressure | Change Pressure | Solvent/g | Catalyst/g | Reaction Time/hr. | Yield GC % o-% | p % | m % | MCH | HAS |
|---|---|---|---|---|---|---|---|---|---|---|---|
| 30 | 225 | 1800 | 200 | H₂O, 30 | 5 g CoCl₂ 8 g CaCl₂ | 20 | 0.9 | 0.9 | 0.6 | — | — |

*prior art

Referring to Table 1, Runs 1, 2 and 3 were an attempt to essentially duplicate the procedures utilized in U.S. Pat. No. 3,532,754, i.e. where a cobalt oxide was supported on sodium carbonate and calcium oxide. The yields were reasonable, and the amount of ring hydrogenation was relatively low, e.g. less than 10%. Run 2 shows that yields were reduced presumably because of the low reaction temperatures employed.

Generally, the results show that one can obtain good yields of toluidine with a modest amount of ring hydrogenation using an unsupported cobalt catalyst where the reaction is carried out in a solvent, either organic or in water. In particular, Runs 25 and 26 show that the unsupported cobalt metal obtained by recovering the cobalt catalyst from Runs 1 and 2 gave essentially the same yield in terms of toluidine produced with similar amounts of methyl cyclohexane. Run 25 shows that the reaction can be carried out in the presence of water, and one does not need the calcium oxide or sodium carbonate support. Other observations can be noted from the data, namely that a basic material needs to be present when the reaction is carried out in an organic medium, e.g. Runs 6–8, and that calcium oxide, or other alkaline earth oxide, would be necessary for reaction in an organic solvent. The examples also show that the presence of alkaline earth oxides substantially inhibit the activity of the cobalt metal when the reaction is carried out in the presence of water (note Run 10, 27, and 28). Results also show that chlorides are particularly detrimental to the reaction (note Runs 29 and 30).

Runs 19, 20, and 21 show that high selectivity to meta toluidine with good conversion to toluidine in general can be achieved by using a prereduced cobalt metal recovered from a previous reaction. These reactions show that the cobalt metal recovered from the previous runs retains its activity and need not be regenerated, other than simple washing with water, for use in the reactant.

What is claimed is:

1. In a process for producing a 1-alkyl amino benzene by the catalytic reduction of an alkyl amino benzene selected from the group consisting of 1-alkyl-2,3-diamino benzene and 1-alkyl-3,4-diamino benzene utilizing a cobalt catalyst, the improvement which comprises:
    forming an aqueous phase containing said alkyl diamino benzene;
    catalytically reducing said alkyl diamino benzene while in the aqueous phase by reacting said alkyl diamino benzene with hydrogen and thereby forming a water insoluble phase containing 1-alkyl amino benzene product and an organic phase containing unreacted alkyl diamino benzene, said reduction carried out in the absence of alkaline earth and alkali metal oxide or carbonate; and
    separating the thus formed water insoluble phase containing 1-alkyl amino benzene product from the aqueous phase.

2. The process of claim 1 wherein said cobalt is present in a proportion of 5 to 50 grams metal per mole of 1-alkyl diamino benzene.

3. The process of claim 2 wherein said alkyl diamino benzene is toluene diamine.

4. The process of claim 3 wherein said 1-alkyl amino benzene produced is toluidine.

5. The process of claim 4 wherein said toluidine is predominately m-toluidine and is formed by utilizing a cobalt ammonia nitrate complex.

6. In a process for producing a 1-alkyl amino benzene by the catalytic reduction of a 1-alkyl diamino benzene selected from the group consisting of 1-alkyl-2,3- and 1-alkyl-3,4-diamino benzene in an inert solvent, the improvement for permitting continuous operation and efficient separation which comprises:
    forming an aqueous phase containing said 1-alkyl diamino benzene;
    reducing the 1-alkyl diamino benzene while in the aqueous phase by reacting said 1-alkyl diamino benzene with hydrogen and thereby forming a water insoluble phase containing 1-alkyl amino benzene product and an aqueous phase containing unreacted 1-alkyl diamino benzene; and
    separating the thus formed water insoluble phase containing 1-alkyl amino benzene product from the aqueous phase.

7. The process of claim 6 wherein said 1-alkyl diamine benzene is toluene diamine and said product is toluidine.

8. The process of claim 6 wherein said cobalt metal is present in a proportion to provide from 1–50 grams metal per mole toluene diamine.

9. The process of claim 8 wherein the cobalt metal is formed by utilizing a cobalt ammonia nitrate complex.

* * * * *